United States Patent
Yamauchi et al.

(10) Patent No.: US 6,274,387 B1
(45) Date of Patent: Aug. 14, 2001

(54) MAGNETIC CARRIER, PREPARATION THEREOF, AND METHOD OF EXTRACTION OF NUCLEIC ACID

(75) Inventors: Syoichi Yamauchi; Kiyoshi Kasai, both of Kanagawa (JP)

(73) Assignee: Tosoh Corporation, Yamaguchi (JP)

( * ) Notice: Subject to any disclaimer, the term of this patent is extended or adjusted under 35 U.S.C. 154(b) by 0 days.

(21) Appl. No.: 09/220,848

(22) Filed: Dec. 28, 1998

(30) Foreign Application Priority Data

Dec. 25, 1997 (JP) .................................................. 9-358064

(51) Int. Cl.[7] ...................... G01N 33/553; G01N 33/552; C12Q 1/68; B01D 35/06
(52) U.S. Cl. .............................. 436/526; 436/527; 435/6; 427/212; 427/213.36; 428/900; 210/222; 210/502; 210/504; 210/506; 210/510.1; 524/457; 524/458; 524/459; 252/62.51
(58) Field of Search ..................................... 436/526, 527; 435/6; 210/222, 502, 504, 506, 510.1; 252/62.51, 62.54, 62.56; 427/212, 213.36; 428/900; 524/457–459

(56) References Cited

U.S. PATENT DOCUMENTS

| | | | |
|---|---|---|---|
| 4,177,253 | * 12/1979 | Davies et al. ............................ | 424/1 |
| 4,694,035 | * 9/1987 | Kasai et al. ............................ | 524/458 |
| 4,716,028 | * 12/1987 | Kasai et al. ............................ | 423/344 |
| 4,742,137 | * 5/1988 | Ono et al. ............................... | 526/92 |
| 4,798,691 | * 1/1989 | Kasai et al. ............................ | 264/47 |
| 4,828,955 | * 5/1989 | Kasai et al. ............................ | 430/111 |
| 4,908,271 | * 3/1990 | Kasai et al. ............................ | 428/402.22 |
| 4,952,651 | * 8/1990 | Kasai et al. ............................ | 526/201 |
| 5,189,107 | * 2/1993 | Kasai et al. ............................ | 525/244 |
| 5,683,875 | * 11/1997 | Lichtenwalter ........................ | 435/6 |
| 5,814,687 | * 9/1998 | Kasai et al. ............................ | 523/223 |
| 5,855,790 | * 1/1999 | Bradburry et al. ................... | 210/676 |
| 5,900,146 | * 5/1999 | Ballard et al. ........................ | 210/222 |
| 6,027,945 | * 2/2000 | Smith et al. ........................... | 436/526 |

FOREIGN PATENT DOCUMENTS

| | | |
|---|---|---|
| 3619303 | 12/1987 | (DE) . |
| 4307262 | 9/1994 | (DE) . |
| 0268243 | 11/1987 | (EP) . |
| 0757106 | 2/1997 | (EP) . |
| 61-181967 | 8/1986 | (JP) .............................. G01N/33/553 |
| 4-501957 | 4/1992 | (JP) .............................. C12N/15/87 |
| 4-501959 | 4/1992 | (JP) .............................. C12N/15/11 |
| 9-19292 | 1/1997 | (JP) .............................. C12N/15/00 |

\* cited by examiner

*Primary Examiner*—Long V. Le
*Assistant Examiner*—Pensee T. Do
(74) *Attorney, Agent, or Firm*—Sughrue, Mion, Zinn, Macpeak & Seas, PLLC

(57) ABSTRACT

A novel magnetic carrier is provided which comprises particulate silica containing a magnetic material, having polyacrylamide on the surface thereof in an amount ranging from 0.3 to 5 mmol/g in terms of monomeric acrylamide. A process for producing the magnetic carrier is also provided in which the surface of particulate silica containing a magnetic material is treated with a coupling agent, and the treated particulate silica is reacted with acrylamide and/or polyacrylamide. The magnetic carrier is useful for extraction of nucleic acid. The magnetic carrier can be produced readily by controlling the shape, the particle diameter, and the pore diameter, and is excellent in strength and adsorption efficiency. The extraction of a nucleic acid can be automated by use of the magnetic carrier.

7 Claims, No Drawings

SEQUENCE LISTING

<160> NUMBER OF SEQ ID NOS: 4

<210> SEQ ID NO 1
<211> LENGTH: 26
<212> TYPE: DNA
<213> ORGANISM: Artificial
<220> FEATURE:
<223> OTHER INFORMATION: Synthetic sequence

<400> SEQUENCE: 1
gtctctgaat cagaaatcct tctatc         26

<210> SEQ ID NO 2
<211> LENGTH: 25
<212> TYPE: DNA
<213> ORGANISM: Artificial
<220> FEATURE:
<223> OTHER INFORMATION: Synthetic sequence

<400> SEQUENCE: 2
catgtcaaat ttcactgctt catcc         25

<210> SEQ ID NO 3
<211> LENGTH: 19
<212> TYPE: DNA
<213> ORGANISM: Artificial
<220> FEATURE:
<223> OTHER INFORMATION: Synthetic sequence

```
<400> SEQUENCE: 3
atccgcaagc accctatca                                              19

<210> SEQ ID NO 4
<211> LENGTH: 21
<212> TYPE: DNA
<213> ORGANISM: Artificial
<220> FEATURE:
<223> OTHER INFORMATION: Synthetic sequence

<400> SEQUENCE: 4
cactccacca tagatcactc c                                           21
```

MAGNETIC CARRIER, PREPARATION THEREOF, AND METHOD OF EXTRACTION OF NUCLEIC ACID

BACKGROUND OF THE INVENTION

1. Field of the Invention

The present invention relates to a magnetic carrier having polyacrylamide on the surface thereof, having controlled properties of a magnetic material content, a particle shape, a particle diameter, and a pore diameter, and being suitable for adsorption and extraction. The present invention also relates to a process for producing the magnetic carrier. The present invention further relates to a method of extraction of a nucleic acid by use of the magnetic carrier.

2. Description of the Related Art

Particulate silica, and the like particulate matters are well known as an adsorbent, and a solid carrier for supporting an adsorbent. The carrier is recovered after use by centrifugation, filtration, or a like operation, which is not convenient. In the adsorption or extraction operation, the objective substance should be isolated from the adsorbate or extract. However, the conventional separation by centrifugation, column separation, or a like method takes a long time, and requires a large apparatus, which is not convenient.

For separation of an objective substance, for example, JP-A-60-244251 ("JP-A" herein means unexamined published Japanese patent application) discloses a method of recovery of objective particles in which a ferromagnetic material is added to the particles and a magnetic field is applied thereto. However, this method has disadvantages that the ferromagnetic material itself may cause self-aggregation in operation of adsorption, extraction, reaction, and so forth, especially under application of a magnetic field, and that the state of the particles cannot be controlled as desired for uniform dispersion for the operation.

For preventing the self-aggregation of ferromagnetic material, JP-A-61-181967 discloses use of a superparamagnetic material as the magnetic material, and Tokuhyo 4-501957 ("Tokuhyo" herein means published Japanese translations of PCT international publication for patent application) discloses use of magnetic particles containing a superparamagnetic material as a solid phase for fixing a sample in separation and analysis of proteins, cells, and DNA. Japanese Patent No. 2554250 discloses a highly movable reagent carrier constituted of a gel matrix having a superparamagnetic reactive substance fixed thereon. In these methods, the superparamagnetic substance is contained in a state of fine micro-particles smaller than the size of the magnetic domains for keeping a magnetic body like iron oxide permanently magnetic, and the particles in a solution are made to aggregate by application of an external magnetic field. By these methods, however, the properties of the magnetic particles are not sufficiently controllable. Therefore, a method is demanded which produces magnetic particles most suitable for the respective uses by controlling the properties thereof, particularly the particle diameter, the pore diameter, the pore volume, and the specific surface area of the magnetic particles, the quantity of the magnetic material in the magnetic particles, and silica concentration of the particle surface.

Particulate silica, for use as an adsorbent or an extractant, is modified preliminarily by introduction of a specific functional group or adsorption of nucleic acid or the like on the surface thereof. For example, the gel for high-speed liquid chromatography is modified by introducing specific functional groups therein. In conventional modification, however, the introduced functional group may come off to cause decrease of the amount of the functional group, resulting in deterioration of the performance as the adsorbent, disadvantageously.

In one method of introduction of polyacrylamide into particulate magnetic silica, the gel is mixed with acrylamide, and the acrylamide is polymerized to deposit the polyacrylamide onto the gel. In this method, the polyacrylamide simply covers the gel without direct bonding between the gel and the polyacrylamide, tending to come off from the gel during operation of adsorption or extraction, disadvantageously.

For formation of a bond between a carrier like the gel and the polyacrylamide, a reaction should be caused between the gel and the polyacrylamide. In the reaction, the polyacrylamide can difficultly be introduced in a specified amount by direct reaction with the functional groups on the gel, and the amount of introduced polyacrylamide is not reproducible. Therefore, a method is demanded for introducing polyacrylamide onto the gel with high reproducibility of the amount of the introduction.

JP-A-9-19292 discloses a method which employs particulate silica as a carrier for adsorbing nucleic acid. In this method, the nucleic acid is considered to be adsorbed onto the particles of silica by hydrogen bonding on the silica surface between the hydroxyl group of the silica particles and the basic group of the nucleic acid. However, the silica particles do not adsorb the nucleic acid in a sufficient amount by the surface thereof, or the amount of the adsorption is not reproducible owing to the steric hindrance by the bulkiness of the nucleic acid.

Tokuhyo 4-501959 discloses molecular oligonucleotide on a magnetic particle surface. In this method, an oligonucleotide having a sequence complementary to the nucleic acid to be adsorbed or extracted should be immobilized onto the magnetic particle surface. Therefore, particulate magnetic material should be provided which has a nucleotide complementary to the objective nucleic acid fixed thereon. For employing this method in clinical testing, many kinds of nucleotide-carrying magnetic particles should be prepared, which poses other problems such as the cost.

In the practice of a clinical test, biological samples such as serum, plasma, and humor may contain infective viruses or bacteria. When the nucleic acid is extracted manually from the sample, the operator is exposed to danger of the infection therewith. Thus, for manual extraction of a nucleic acid, the procedure is preferably simple, and is less liable to cause evolution of aerosol or the like from the sample, or more preferably the operation is automated. However, a conventional process of nucleic acid extraction is complicated and cannot readily be automated.

After comprehensive study to solve the above problems, it was found by the inventors of the present invention that silica particles containing a magnetic material (hereinafter referred to as "particulate magnetic silica") are improved by introducing a prescribed amount of polyacrylamide thereto and adjusting the properties to increase the adsorption capacity and the adsorption speed to be suitable for an adsorbent and extractant for various uses. It was also found that the polyacrylamide-containing particulate magnetic silica can be produced readily by reacting the particulate magnetic silica with a coupling agent and then reacting it with acrylamide and/or polyacrylamide. Further, it was found that a nucleic acid in a biological sample can be extracted readily and effectively by use of the particulate magnetic silica thus prepared. Consequently, the present invention has been accomplished.

SUMMARY OF THE INVENTION

An object of the present invention is to provide a magnetic carrier which has controlled properties of a magnetic substance content, a shape, a particle diameter, and a pore diameter without the above disadvantages of the prior art.

Another object of the present invention is to provide a simplified process for producing the above magnetic carrier.

A further object of the present invention is to provide a simplified automatable method of extraction of a nucleic acid with the above magnetic carrier.

The magnetic carrier of the present invention comprises particulate silica containing a magnetic material, and has polyacrylamide on the surface thereof in an amount ranging from 0.3 to 5 mmol/g in terms of monomeric acrylamide.

The process for producing the magnetic carrier of the present invention comprises the steps of (a) providing particulate magnetic silica by addition of a magnetic material to silica or a silica source material; (b) reacting the particulate magnetic silica after the step (a) with a coupling agent; (c) washing the particulate magnetic silica after the step (b); (d) reacting the particulate magnetic silica after the step (c) with acrylamide and/or polyacrylamide; and (e) washing and drying the particulate magnetic silica after the step (d).

The method of extraction of nucleic acid of the present invention comprises mixing the above magnetic carrier with a sample to allow the nucleic acid in the sample to be adsorbed on the magnetic carrier, and separating the magnetic carrier from the sample by utilizing a magnetic force.

DETAILED DESCRIPTION OF THE PREFERRED EMBODIMENT

The nucleic acid in the present invention means DNA (deoxyribonucleic acid) and/or RNA (ribonucleic acid), which may be single-stranded or double-stranded, and may be a mixture thereof.

Present invention is described below in detail.

The magnetic carrier of the present invention comprises particulate silica containing a magnetic material, and has polyacrylamide on the surface thereof. The materials constituting the magnetic carrier are described below.

Magnetic Material

The magnetic material used for constituting the magnetic carrier of the present invention may be any material which has a magnetic force. Of magnetic materials, preferred are superparamagnetic materials which are magnetized strongly on application of a magnetic field, and demagnetized on removal of the magnetic field. The superparamagnetic materials include spinel ferrite, plumbite ferrite, and alloys mainly composed of iron, nickel, cobalt, or the like. For introducing the magnetic material uniformly into the particulate silica, a magnetic fluid is preferably used which is prepared by suspending ultra-fine particles of magnetite or ferrite in water or an organic solvent.

Particulate Silica

The particulate silica for the magnetic carrier of the present invention is a polymer constituted by bonding of Si (silicon) and O (oxygen), including silica gel, silica glass, quartz glass, silicon oxide, and silicate salts. Of these, silica gel is preferred because of the relatively large specific surface area, and ease of controlling the pore structure thereof. These materials are preferably a synthesized product for less influence of an impurity in the process of extraction or adsorption of the nucleic acid. However, natural materials may be used after purification.

The average particle diameter of the particulate silica ranges preferably from 1 to 200 μm. Within this range, the magnetic material can be introduced in a larger amount into the particulate silica, the separation by use of the magnetic carrier can be conducted in a shorter time, and the gel keeps its shape stably with less likelihood of destruction in practical use which is advantageous. More preferably the average particle diameter ranges from 1 to 20 μm for higher dispersibility in a sample-containing solution by stirring with less sedimentation tendency. In particular, within the average particle diameter ranging from 4 to 20 μm, the particle size is appropriate, and the magnetic carrier of the present invention can readily be separated from the sample-containing solution, and is excellent in magnetic collectibility, shape stability, dispersibility in a solution, and separability from a solution.

The average pore diameter of the particulate silica ranges preferably from 1 to 200 nm for particle shape stability, and higher adsorption capacity, and higher adsorption speed and higher reaction efficiency in adsorption or extraction. More preferably, the average pore diameter ranges from 1 to 100 nm for retention of sufficient strength of the particles in practical use for a long term, still more preferably from 1 to 80 nm for retention of particle strength for a longer term.

The pore volume of the particulate silica ranges preferably from 0.1 to 2.5 mL/g based on dry weight for particle shape stability, and higher adsorption capacity, higher adsorption speed and higher reaction efficiency in adsorption or extraction. More preferably, the pore volume ranges from 0.1 to 1.5 mL/g for retention of appropriate strength of the particles in practical use for a long term in addition to the above effects, still more preferably from 0.1 to 1.2 mL/g for retention of particle strength for a longer term.

The BET specific surface area of the particulate silica ranges preferably from 10 to 800 $m^2/g$ based on dry weight for particle shape stability, and higher adsorption capacity, higher adsorption speed and higher reaction efficiency in adsorption or extraction. More preferably, the BET specific surface area ranges from 10 to 400 $m^2/g$ for retention of sufficient strength of the particles in practical use for a long term.

Particulate Magnetic Silica

The particulate magnetic silica used for the magnetic carrier in the present invention is composed of the magnetic material and the particulate silica mentioned above. The process of preparation thereof is not specially limited. The process includes, for example, a first method in which an Si alkoxide is converted to an Si alkoxide polymer, and the polymer is allowed to gel together with a magnetic material by addition of an alkali; a second method in which a magnetic material is added to particulate silica such as silica gel by immersion; and a third method in which an alkali silicate is added to a magnetic material, and an acid is added thereto to form a gel.

The content of the magnetic material in the particulate magnetic silica ranges preferably from 5 to 50% by weight of the particulate magnetic silica. Within this content range, the obtained particulate magnetic silica has sufficient magnetic properties for practical uses to exhibit excellent effects; the magnetic material does not aggregate so much, and can be introduced uniformly into the particles of silica; and the control of the spherical shape and porosity of the silica particles, and modification of the particle surface by polyacrylamide are facilitated. More preferably, the content of the magnetic material ranges from 5 to 25% by weight in the particulate magnetic silica. Within this lower concentration range, besides the above effects, sufficient magnetic properties are obtained, and the concentration of silica component is increased corresponding to the lower content of the magnetic material, facilitating control of the particle shape and the porosity.

Magnetic Carrier

The magnetic carrier of the present invention is constituted of the particulate magnetic silica having at least polyacrylamide bonded on the surface thereof. More specifically, the magnetic carrier is prepared by polymerizing acrylamide and/or polyacrylamide on the particulate magnetic silica to bond the acrylamide and/or polyacrylamide to the surface of the particles, or by bonding polyacrylamide to the particulate magnetic silica. Therefore, the final magnetic carrier has polyacrylamide at least on the surface of the carrier. The surface herein means the outermost face of the particles, but includes the surface of the pores, if pores are present in the interior of the particles.

The content of the polyacrylamide in the magnetic carrier of the present invention ranges preferably from 0.3 to 5 mmol/g based on dry weight. The content of the polyacrylamide is measured by determination of N (nitrogen) by elemental analysis or other means, and is represented by moles of N in one gram of the magnetic carrier since the number of moles of N is equal to the number of moles of acrylamide monomer. Therefore, the content of the polyacrylamide in the magnetic carrier is shown by the total amount of the acrylamide and the polyacrylamide contained in the magnetic carrier. Within this content range, the amount of acrylamide is appropriate for exhibiting effects of the amide groups of the acrylamide and polyacrylamide effectively, and the strength is practically satisfactory without excess acrylamide and polyacrylamide. Furthermore, within the content range of 0.5 to 3.0 mmol/g, the amount of the introduction of the polyacrylamide by synthesis is reproducible, so that the performance of adsorption or extraction is reproducible with confidence. More preferably, the content is in the range from 1.0 to 3.0 mmol/g for higher stability of the adsorption and extraction performance.

The average particle diameter of the magnetic carrier of the present invention ranges from 1 to 200 $\mu$m. Within this range, the magnetic material can be introduced in a larger amount into the carrier, the separation by use of the magnetic carrier can be conducted in a shorter time, and the shape of the carrier particles is stable without gel destruction in practical use. More preferably the average particle diameter of the magnetic carrier ranges from 1 to 20 $\mu$m for higher dispersibility in a sample-containing solution to maintain dispersion with stirring with less sedimentation tendency, in addition to the above effects. In particular, within the average particle diameter in the range from 4 to 20 $\mu$m, the final magnetic carrier can readily be separated from the sample-containing solution, and is excellent in magnetic collectibility, shape stability, dispersibility in a solution, and separability from a solution.

The average pore diameter of the magnetic carrier of the present invention ranges preferably from 1 to 200 nm for particle shape stability, and higher adsorption capacity, and higher adsorption speed and higher reaction efficiency in adsorption or extraction. More preferably, the average pore diameter ranges from 1 to 100 nm for retention of sufficient strength of the particles in practical use for a long term, still more preferably from 1 to 80 nm for retention of particle strength for a longer term.

The pore volume of the magnetic carrier of the present invention ranges preferably from 0.1 to 2.5 mL/g based on dry weight for particle shape stability, and higher adsorption capacity, higher adsorption speed and higher reaction efficiency in adsorption or extraction. More preferably, the pore volume ranges from 0.1 to 1.5 mL/g for retention of suitable strength of the particles in practical use for a long term besides the above effects, still more preferably from 0.1 to 1.2 mL/g for retention of particle strength for a longer term.

The BET specific surface area of the magnetic carrier of the present invention ranges preferably from 10 to 800 $m^2/g$ based on dry weight for particle shape stability, and higher adsorption capacity, higher adsorption speed and higher reaction efficiency in adsorption or extraction. More preferably, the BET specific surface area ranges from 10 to 400 $m^2/g$ for retention of sufficient strength of the particles in practical use for a long term.

The content of the magnetic material in the magnetic carrier is lower than that of the particulate magnetic silica by the amount of the introduced polyacrylamide, usually by about 10% to 20%.

The magnetic carrier of the present invention is useful for adsorption-separation or extraction of nucleic acids. The term "adsorption-separation" herein means adsorption of the nucleic acid by the magnetic carrier from a reaction solution and its subsequent separation from the reaction solution. The term "extraction" herein means adsorption of nucleic acid by the magnetic carrier and subsequent elution of the adsorbed nucleic acid from the magnetic carrier to obtain objective nucleic acids.

The magnetic carrier of the present invention, for adsorption-separation or extraction of a nucleic acid from a solution, has an average particle diameter ranging preferably from 1 to 20 $\mu$m, more preferably from 1 to 15 $\mu$m, still more preferably from 3 to 10 $\mu$m in consideration of dispersibility for ease of operation and of separation performance of the magnetic carrier. The magnetic carrier having an average diameter of less than 1 $\mu$m may take longer time for separation owing to excessively small particle diameter, whereas the magnetic carrier having an average diameter of larger than 20 $\mu$m may not give stable performance owing to low dispersion stability in the nucleic acid-containing solution, and the magnetic carrier having an average particle diameter larger than 200 $\mu$m tends to sediment more readily to make the operation more troublesome.

The polyacrylamide content of the magnetic carrier of the present invention ranges preferably from 0.5 to 5 mmol/g based on dry weight. Within this polyacrylamide content, the properties of the amide group of the acrylamide and the polyacrylamide are effectively exhibited, and the strength is sufficient for the intended use owing to the suitable amount of the introduced polyacrylamide. More preferably, in the range of the polyacrylamide content from 0.5 to 3.0 mmol/g, the polyacrylamide can be introduced with high reproducibility, besides the above effects. Still more preferably, in the range of the polyacrylamide content from 1.0 to 3.0 mmol/g, the performance in adsorption and extraction is more stable.

The amount of the nitrogen atoms existing on the surface of the magnetic carrier of the present invention is preferably not lower than 5 atom % for high performance and its reproducibility in adsorption-separation and extraction of a nucleic acid. In this range of the nitrogen atom content, the surface of the magnetic carrier is covered almost entirely with polyacrylamide to give stable performance including the adsorption capacity. More preferably, the amount of the nitrogen atoms on the surface ranges from 5 to 10 atom % to utilize the magnetic carrier surface effectively for a large molecular nucleic acid in adsorption-separation and extraction of a nucleic acid, and to utilize the polyacrylamide effectively for covering sufficiently and not excessively the surface of the magnetic carrier. The amount of the nitrogen atoms on the magnetic carrier surface is determined, for example, by measuring the surface nitrogen atoms by X-ray photoelectron spectroscopy.

Production of Magnetic Carrier

The process for producing the magnetic carrier of the present invention comprises (1) Step (a) of addition of a magnetic material to silica or a silica source material to produce particulate magnetic silica, and (2) Steps (b) to (e) of introduction of polyacrylamide to the particulate magnetic silica. The steps of the production are described below successively.

[(1) Step of Producing Particulate Magnetic Silica]

The particulate magnetic silica for producing the magnetic carrier of the present invention can be produced by any known process. However, it can be produced more readily by the process comprising the steps below.

(i) Hydrolysis of a Si alkoxide by an acid to obtain a Si alkoxide polymer, (ii) Addition of a magnetic material to the Si alkoxide polymer, (iii) Dispersion of a solution of a mixture of the Si alkoxide polymer and the magnetic material in a state of spheres in water, and its conversion into a gel by alkali, and (iv) Washing of the gel with water, substitution of the water with a solvent such as an organic solvent or mixture of water and organic solvent, and drying of the gel.

Any Si alkoxide which is capable of forming a polymer by hydrolysis is useful in the production process in the present invention without limitation. The Si alkoxide includes $Si(OCH_3)_4$, $Si(OCH_2H_5)_4$, $Si(O-n-C_3H_7)_4$, $Si(O-i-C_3H_7)_4$, $Si(O-n-C_4H_9)_4$, and $Si(O-i-C_4H_9)_4$. Another metal alkoxide may be added thereto.

In the above steps, the Si alkoxide is partially hydrolyzed in an acidic solution to an extent not to form a gel. The acidic solution is preferably a mixture of an acid, water, and an organic solvent.

After the partial hydrolysis, the Si alkoxide in the solution is polymerized. The polymerization degree of the Si alkoxide polymer can be controlled by adjusting the amount of water, the polymerization temperature, the polymerization time, and other polymerization conditions. The viscosity of the Si alkoxide polymer depends on the polymerization degree, the viscosity being higher with the higher polymerization degree. The polymerization degree is controlled to obtain the reaction solution viscosity of not lower than 10 centipoise but not to cause gelation. The viscosity can be measured, for example, according to JIS-K-7117–1987 at 25° C.

The resulting Si alkoxide polymer solution may be diluted with an organic solvent. When the polymer is diluted with an organic solvent, the concentration of the Si alkoxide polymer is controlled preferably to be not lower than 20% by weight based on the total diluted solution to obtain spherical gel particles.

In place of the Si alkoxide polymer obtained above, commercial particulate silica may be used without treatment.

Subsequently, a magnetic material is added to the Si alkoxide polymer. The magnetic material may be used in a state of dispersion or solution in water or in an organic solvent. As the magnetic material, a magnetic fluid is preferred in view of the dispersibility in the Si alkoxide polymer. The magnetic fluid may be a commercial product without treatment or may be used after solvent substitution treatment.

Then the mixture of the Si alkoxide polymer or its diluted solution and the magnetic material is dispersed in a state of spheres in water with stirring. A dispersing agent such as a surfactant, and polyvinyl alcohol, may be added to the water for dispersing the mixture.

The formed spheres are converted into gel particles by addition of a basic material to the mixture.

The formed gel particles are collected by filtration, centrifugation, or a like known process, washed with water, and dried. The water for washing may be usual water or usual hot water.

To avoid constriction or aggregation of the gel by direct evaporation of water from the surface and the interior of the gel, the water is substituted preferably by an organic solvent before the drying.

As described above, the magnetic silica gel is prepared for the magnetic carrier of the present invention.

[(2) Steps of Introducing Polyacrylamide to Particulate Magnetic Silica to Obtain Magnetic Carrier]

The magnetic carrier can be produced from the particulate magnetic silica by any known process. The magnetic carrier can be produced more readily by the process shown below.

(b) Reaction of the particulate magnetic silica with a coupling agent, (c) Washing of the particulate magnetic silica containing the introduced coupling agent after Step (b), (d) Reaction of the particulate magnetic silica after Step (c) with acrylamide and/or polyacrylamide, (e) Washing and drying of the particulate magnetic silica after Step (d).

Any particulate magnetic silica may be used which contains magnetic material in the present invention.

The magnetic carrier of the present invention is produced by reaction of a coupling agent with the surface of the particulate magnetic silica, and subsequently introducing polyacrylamide into the particulate magnetic silica by reaction of acrylamide and/or polyacrylamide therewith.

The coupling agent used in the present invention is not limited, provided that it is capable of bonding to the silanol group represented by Formula (1) present on the surface of the particles of the magnetic silica and capable simultaneously of bonding to acrylamide and/or polyacrylamide. The coupling agent may be a single compound or a combination of two or more compounds. The coupling agent in the present invention is preferably the one which introduces any of a vinyl group represented by Formula (2), a methacryl group represented by Formula (3), and an epoxy group represented by Formula (4). The introduced group reacts with acrylamide represented by Formula (5) or polyacrylamide represented by Formula (6) to produce the magnetic carrier of the present invention. The polyacrylamide herein includes polymerization products of two or more molecules of monomeric acrylamide.

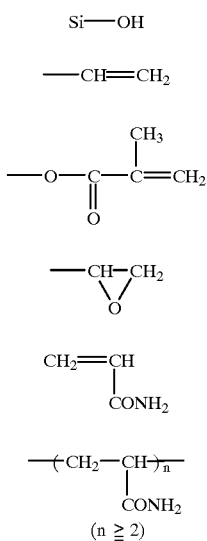

More specifically, the coupling agent employed in the present invention may be any compound which is capable of bonding to acrylamide and/or polyacrylamide in the production process described below. The coupling agent includes silane coupling agents containing a vinyl group, a methacryl group, or an epoxy group such as vinyltrichlorosilane, trimethoxyvinylsilane, triethoxyvinylsilane, tris(2-methoxyethoxy)vinylsilane, 3-glycidoxypropyltrimethoxysilane, 3-methacryloxypropyltrimethoxysilane, and diethoxy-3-glycidoxypropylmethyllsilane. These coupling agent may be used singly or in combination of two or more thereof.

Two or more different kinds of compounds may be employed combinedly as the coupling agent. In this case, one coupling agent (A) introduces a functional group through the silanol on the surface of the particles of magnetic silica, and then another coupling agent (B) introduces a vinyl, methacryl, or epoxy group to the introduced functional group.

The coupling agent is preferably a single compound for simplicity of the production process of the magnetic carrier of the present invention.

In production of the magnetic carrier, the aforementioned particulate magnetic silica is dried to remove adsorbed water. The adsorbed water is desirably removed as completely as possible, to a water content of not more than 5% by weight. The dried particulate magnetic silica and a coupling agent are mixed with stirring in an organic solvent. Then an acid, a base, or both an acid and a base are added to cause reaction between the particulate magnetic silica and the coupling agent. The solvent employed is selected preferably from hydrocarbons such as benzene, toluene, cyclohexane and hexane. The acid for the reaction includes phenols, and organic acids such as formic acid, and acetic acid. The base for the reaction includes organic basic compounds such as amines and ureas. The mixture solution is preferably stirred at a temperature ranging from 30 to 90° C. for a time of 30 minutes to 6 hours for uniform reaction of the particulate magnetic silica with the coupling agent.

Subsequently, the particulate magnetic silica containing the introduced coupling agent is washed to remove the unreacted coupling agent. For the removal, the particulate magnetic silica containing the coupling agent is collected by filtration, centrifugation, or a like process. The collected particulate magnetic silica is mixed with an organic solvent, and then is collected again. This operation is preferably repeated two to five times. Then the washed particulate magnetic silica is preferably dispersed in a solvent to be used in Step (c), and collected. This operation is repeated one to four times. The collection by filtration may be conducted by a conventional method.

In the subsequent step, the particulate magnetic silica after treatment with the coupling agent is reacted with acrylamide and/or polyacrylamide. The acrylamide and/or polyacrylamide may be directly reacted with the particulate magnetic silica. However, the acrylamide and/or polyacrylamide is preferably polymerized during the reaction with the particulate magnetic silica to increase the amount of the introduction or to control the molecular weight of the polyacrylamide. In this reaction, monomeric acrylamide is preferably used, since the production is made easier and the acrylamide bonded to the silica particle surface is expected to be polymerized into a linear polymer. In particular, for extraction of a nucleic acid which is a linear molecule, the linear polyacrylamide is expected to be more suitable. The introduction of the acrylamide to the silica particle surface is conducted by any polymerization, preferably by radical polymerization.

The solvent for the above reaction is preferably selected from water, alcohols, and mixtures of water and an alcohol. The alcohol is preferably water-soluble, and includes methanol, ethanol, 1-propanol, 2-propanol, 1-butanol, and 2-butanol.

The reaction medium is preferably oxygen-free, or contains dissolved oxygen at a low concentration, preferably ranging from 0 to 1 mg/L.

The reaction is conducted by mixing particulate magnetic silica, acrylamide and/or polyacrylamide, and an initiator. The initiator includes azo initiators such as azoisobutylonitrile, inorganic peroxide initiators such as potassium persulfate, and ammonium persulfate, and organic peroxide initiators such as benzoyl peroxide, and di-t-butyl peroxide, as simple initiators; and combination of hydrogen peroxide and ferrous salt, as binary initiators.

For uniform reaction of particulate magnetic silica with acrylamide and/or polyacrylamide, a solution containing the coupling agent-treated particulate magnetic silica, acrylamide and/or polyacrylamide, and an initiator is stirred at a temperature from 30 to 90° C. for a time from 30 minutes to 24 hours. The polyacrylamide remaining in the solution after the reaction has a number-average molecular weight ranging preferably from 1,000 to 1,000,000. When the polyacrylamide in the solution after the reaction has a number-average molecular weight of lower than 1,000, the reaction may have not proceeded sufficiently between the functional group introduced to the particulate magnetic silica and acrylamide and/or polyacrylamide. On the other hand, when the polyacrylamide in the solution after the reaction has a number-average molecular weight of higher than 1,000,000, the viscosity of the solution is too high to introduce the polyacrylamide uniformly to the particulate magnetic silica.

The resulting magnetic carrier is washed to remove unbonded acrylamide and polyacrylamide. The magnetic carrier is collected by filtration, centrifugation, or a like operation, and washed in a conventional manner. The solvent for the washing includes usual cold water, hot water, hydrophilic alcohols such as methanol, ethanol, and propanol, and mixtures of water and an alcohol. This removal operation removes the unbonded acrylamide and polyacrylamide as completely as possible to prevent the bonding of the adsorption object thereto. The acrylamide and polyacrylamide not bonded to the particulate magnetic silica are present preferably at a content of not more than 1 ppm in the magnetic carrier.

The washed magnetic carrier is dried by a conventional manner to obtain a dried magnetic carrier of the present invention.

Before the drying, the magnetic carrier may be treated for solvent substitution, since direct evaporation of water from the surface and the interior of the gel may cause constriction, aggregation, or destruction of the gel. In the solvent substitution treatment, the water in the gel is substituted by an organic solvent, and thereafter the organic solvent is removed by heating. The organic solvent has preferably a surface tension lower than that of water, and is preferably miscible with water at any mixing ratio. Water has a surface tension of 72 dyn/cm (dyn/cm=$10^{-3}$Nm$^{-1}$) in the air at 25° C. according to the Wilhelm method. An organic solvent having a surface tension lower than this is selected. The organic solvent includes formamide, N,N-dimethylformamide, ethylene glycol, propylene glycol, methanol, ethanol, 1-propanol, 2-propanol, 1-butanol, 2-butanol, 1-pentanol, and 2-pentanol. The water or the solvent is evaporated at atmospheric pressure, but may be evaporated under a reduced pressure.

In the above process, the particulate magnetic silica having the introduced polyacrylamide, after washing, can be stored without drying in the same solvent as that used for the washing.

In the introduction of the polyacrylamide, with increasing amount of the addition of polyacrylamide to the magnetic carrier, the introduced polyacrylamide comes to be saturated at a certain limit according to measurement of nitrogen atoms by X-ray photoelectron spectroscopy. From this fact, in the magnetic carrier of the present invention, the polyacrylamide is considered to come to be bonded, with increase of the amount of the polyacrylamide, to a certain amount to cover nearly entirely the surface of the particle of the magnetic silica.

The magnetic carrier of the present invention is prepared in the manner as described above.

The magnetic carrier of the present invention is useful for adsorption and extraction of sugars, low molecular hydrophobic organic compounds, and nucleic acids. The magnetic carrier is useful also as a carrier in analysis measurement of nucleic acids, sugars, and so forth, and as a carrier in separating means such as affinity chromatography for sugars, low molecular hydrophobic organic compounds, nucleic acids, and the like.

In particular, in use for adsorption and extraction of nucleic acids, the magnetic carrier of the present invention is mixed with a sample containing a nucleic acid to adsorb the nucleic acid in the sample, and the magnetic carrier is separated by utilizing a magnetic force from the sample to extract readily the nucleic acid. From the magnetic carrier after the extraction, the nucleic acid is desorbed by addition of a desorption solvent such as water to separate the nucleic acid. The nucleic acid separated by desorption is amplified directly or by polymerase chain reaction, whereby the quantity of the nucleic acid can be determined.

As described above, the magnetic carrier of the present invention is useful for adsorption and extraction of nucleic acids. This is considered to be for the seasons below. The magnetic carrier of the present invention has polyacrylamide on the surface, so that the polar functional groups such as an amide group capable of interacting with a nucleic acid are fixed not only on the surface of the carrier, but extend as high molecular polyacrylamide chains apart from the surface of the carrier with the end of the polyacrylamide molecule bonded to the carrier surface. Therefore, the active sites of interaction with the high molecular nucleic acid is increased, and the once formed interaction is firmly held by superposition with the polyacrylamide. However, the above consideration does not limit the present invention.

EXAMPLES

The present invention is described below in more detail by reference to Examples without limiting the invention in any way. The evaluations are conducted as shown below.

The particulate magnetic silica used in Examples was superparamagnetic according to measurement of magnetic hysteresis by a vibrating sample magnetometer (Model BHV-50, manufactured by Riken Denshi K.K.).

Magnetic Material Content

For determination of Si, the particulate magnetic silica was decomposed by aqua regia, and treated with perchlorate, and the content was determined by gravimetric analysis. For determination of Fe (iron), the particulate magnetic silica was decomposed by nitric acid-hydrofluoric acid, and treated with perchlorate, and the content was determined by ICP emission spectrometry.

Average Particle Diameter

The sample was dispersed in water, and the dispersion was subjected to measurement with a particle size distribution tester LS-130 (manufactured by Coulter Co.). The size was represented by a volume-average particle diameter.

Average Pore Diameter and Pore Volume

The measurement was conducted by a mercury penetration method by application of a pressure ranging from 0 to 207 MPa with Pore Sizer 9320 (manufactured by Micromeritics Co.).

BET Specific Surface Area

The measurement was conducted by a BET one-point method with Monosorb (manufactured by US Quanatachrome Co.).

Surface Analysis

Fe, Si, N, C, and O on the surface of the sample particle were determined by an X-ray photoelectron spectrometer (ESCA 5400MC, manufactured by Perkin-Elmer Co.). The composition was represented by surface element composition (atom %) relative to the total amount (100%) of Fe, Si, N, C, and O.

N Content (Polyacrylamide Content)

Nitrogen was determined with an elemental analysis apparatus.

Dissolved Oxygen Concentration

The dissolved oxygen concentration in the reaction solution was measured with a dissolved oxygen concentration tester (Model UC-12, manufactured by Central Kagaku Co.).

Polymerization Degree of Polyacrylamide

The polymerization degree of the polyacrylamide was measured with a set of high performance liquid chromatography apparatuses (AS-8000, CCPM, CO-8010, RI-8010, and SC-8010, manufactured by Tosoh Corporation) by use of a standard polyethylene oxide kit (produced by Tosoh Corporation) as the standard of the molecular weight. The molecular weight was represented by a number-average molecular weight.

Nucleic Acid Extraction Performance (Typical Method)

The nucleic acid employed was pAW 109 DNA (produced by Perkin Elmer Co.) at a sample concentration of $2 \times 10^7$ molecules/mL.

To 200 µL of the nucleic acid sample solution, was added 400 µL of extracting solid phase-containing liquid shown below. The mixture was stirred at room temperature for 10 minutes. Then the magnetic carrier was gathered to the corner of the vessel by use of a magnet, and the solution was removed by suction. The remaining gel was again suspended in 0.4 mL of washing solution (aqueous 40 vol % isopropanol solution) which was added thereto. Then the gel was gathered again to the vessel corner with a magnet, and the solution was removed by suction. The magnetic carrier was suspended in 200 µL of elution solution (water), and gel was gathered to the corner of the vessel, and the elution solution was taken out by suction. The solution was vacuum-dried to obtain a solid matter. This solid matter was re-dissolved in 200 µL of water. A 50 µL fraction of this solution was subjected to a polymerase chain reaction (hereinafter referred to as "PCR") in the manner shown below.

The magnetic carrier was added in an amount of 2.5 mg/mL in aqueous 50 vol % isopropanol to prepare the aforementioned extracting solid phase-containing liquid. Two primers were used: Sequence No. 1 and Sequence No. 2 shown later. In the PCR reaction solution composition, the nucleic acid of Sequence No. 1 was 0.2 µM-Forward Primer DM 151, the nucleic acid of Sequence No. 2 was 0.2 µM-Reverse Primer DM 152, and other components were 2.2 mM-$MgCl_2$, 0.29 mM-dNTP, and Taq polymerase (AmpliTaq Gold) 2.25 units/75 µL). It was subjected to PCR at 95° C. for 10 minutes 45 seconds, and of 45 cycles of 95° C. for 15 seconds and 60° C. for 30 seconds, and thereafter at 72° C. for 7 minutes. After completion of the PCR, a part of the reaction solution was subjected to agarose electrophoresis and the presence of the intended size of bands was examined visually.

The above extraction test was repeated ten times for each of the samples. The ratio of detection of the extracted nucleic acid (bands of intended size) was shown as the detection ratio as a measure of the nucleic acid extraction.

Detection ratio (%)=[(Times of detection of extracted nucleic acid)/(Total number of times of extraction tests)]×100

Example 1

A solution mixture of 150.0 g of $Si(OC_2H_5)_4$ and 62.7 g of ethanol was stirred at 40° C. for 30 minutes. To the solution, 14.9 g of aqueous 1/100-N hydrochloric acid solution was added dropwise with stirring at a temperature of 40° C. The solution was stirred for 1 hour, and then at 90° C. for 4 hours, and at 165° C. for 12 hours with removal of distillate to obtain an Si alkoxide polymer. The above operation was conducted in a nitrogen atmosphere. The obtained Si alkoxide polymer had a viscosity of 50 centipoises at room temperature according to the aforementioned measurement method. 70.0 Grams of the obtained Si alkoxide polymer was dissolved in 70.0 g of 1-pentanol. Thereto, 20 mL of a commercial magnetic fluid (produced by Ferro Tech K.K.: containing 35% by weight of a magnetic material, 10% by weight of a surfactant, and the balance of 1-butanol (total 100%) was added to obtain a uniform solution. This solution was added to 560.0 g of aqueous 5% polyvinyl alcohol kept at 80° C. with stirring. After stirring the mixture for 30 minutes, 12.5 mL of aqueous 5 wt % $NH_4OH$ was added thereto. The mixture was stirred at 80° C. for 3 hours. The resulting liquid suspension was poured into 1000 mL of hot water of 70° C. The formed solid was collected by filtration and washed with warm water. After washing, the solvent was replaced three times with 2-propanol, and the solid was vacuum-dried to obtain spherical particulate magnetic silica.

Ten grams of this particulate magnetic silica was dried at 150° C. for 15 hours. The dried silica was added to 100 mL of toluene, and the mixture was stirred. To the solution were added 4 mL of 3-methacryloxypropyltrimethoxysilane, 0.7 mL of dimethylaminoethanol, and 50 µL of phenol, and the mixture was stirred. After stirring at 85° C. for 3 hours, this solution was filtered to obtain a particulate magnetic silica having the 3-methacryl group. This silica was washed with 50 mL of toluene, and was subjected to filtration twice to obtain a particulate magnetic silica having the 3-methacryl group. It was washed with 50 mL of methanol and filtered three times, and further washed with 50 mL of an aqueous 40 vol % methanol solution and filtered twice. This particulate magnetic silica was added to 100 mL of an aqueous 40 vol % methanol solution, and was stirred. To the solution, were added 9 g of acrylamide monomer, and 0.3 g of potassium persulfate, and the mixture was stirred. This solution was stirred at 60° C. for 15 hours under a nitrogen stream of 50 mL/min. Thereto, 200 mL of warm water was added. The reaction solution was centrifuged to obtain a precipitate containing a magnetic carrier modified with polyacrylamide. The precipitate was washed with 100 mL of warm water and filtered four times. Further the solvent substitution and filtration was conducted three times by use of 50 mL of 2-propanol. The treated precipitate was vacuum dried to obtain a magnetic carrier.

The obtained magnetic carrier was subjected to measurement of the polyacrylamide content (moles in terms of monomeric acrylamide), the particle diameter, the amount of nitrogen atoms on the surface, the average pore diameter according to a mercury penetration method, the pore volume, the average molecular weight of the polyacrylamide in the reaction solution, and the dissolved oxygen in the reaction solution, according to the measurement methods described above. Table 1 show the measurement results. The obtained polyacrylamide-bonded particulate magnetic silica (magnetic carrier) was evaluated for nucleic acid extraction performance. Table 2 shows the results. The band of the intended size was observed with this magnetic carrier to show the nucleic acid extraction performance. The detection ratio was 100%. Thus the nucleic acid extraction was conducted with sufficient reproducibility.

Example 2

A polyacrylamide-bonded particulate magnetic silica (magnetic carrier) was prepared in the same manner as in Example 1 except that 3-methacryloxypropyltrimethoxysilane was replaced by triethyoxyvinylsilane. The obtained magnetic carrier contained polyacrylamide at a molar content of 1.4 mmol/g in terms of monomeric acrylamide on dry weight basis. The obtained magnetic carrier was evaluated in the same manner as in Example 1. Table 1 shows the results. This magnetic carrier was evaluated for nucleic acid extraction performance in the same manner as in Example 1. Table 2 shows the results. The nucleic acid extraction performance of this magnetic carrier was confirmed by the presence of the band of the intended size in the performance test. The detection ratio was 100%. Thus, the nucleic acid extraction was conducted with sufficient reproducibility.

Example 3

A polyacrylamide-bonded particulate magnetic silica (magnetic carrier) was prepared in the same manner as in Example 1 except that 3-methacryloxypropyltrimethoxysilane was replaced by dimethoxy-3-glycidoxypropylmethylsilane. The obtained magnetic carrier contained polyacrylamide at a molar content of 3.5 mmol/g in terms of monomeric acrylamide on dry weight basis. The obtained magnetic carrier was evaluated in the same manner as in Example 1. Table 1 shows the results. This magnetic carrier was evaluated for nucleic acid extraction performance in the same manner as in Example 1. Table 2 shows the results. The nucleic acid extraction performance of this magnetic carrier was confirmed by the presence of the band of the intended size in the performance test. The detection ratio was 100%. Thus, the nucleic acid extraction was conduced with sufficient reproducibility.

Comparative Example 1

The particulate magnetic silica before the modification with a coupling agent in Example 1 without further treatment was tested for nucleic acid extraction performance in the same manner as in Example 1. The results are shown in Table 1. With this particulate magnetic silica, extraction of the nucleic acid was confirmed, but the density of the band of the intended size was low, and the detection ratio was as low as 20% with low reproducibility with unstable performance.

Comparative Example 2

A particulate magnetic silica which has a 3-methacryl group introduced by use of a 3-methacryloxypropyltrimethoxysilane in the same manner as in Example 1 was used without further treatment. Table 1 shows the properties of the particulate magnetic silica. This particulate magnetic silica was tested for the nucleic acid extraction performance in the same manner as in Example 1. Table 2 shows the results. The nucleic acid could not be extracted with this particulate magnetic silica, the detection ratio being zero percent.

From comparison of Comparative Examples 1 and 2 with Examples, the particulate magnetic silica having no polyacrylamide introduced exhibited low efficiency of nucleic acid extraction. Introduction of a 3-methacryl group to the particulate magnetic silica lowers further the efficiency of nucleic acid extraction. Further introduction of polyacrylamide to this particulate magnetic silica will give the nucleic acid extraction performance.

Comparative Example 3

A polyacrylamide-bonded particulate magnetic silica was prepared in the same manner as in Example 1 except that the reaction of the particulate magnetic silica having a 3-methacryl group (the properties are shown in Table 1) and acrylamide was conducted in the air. The obtained magnetic carrier contained polyacrylamide at a molar content of 0.2 mmol/g in terms of monomeric acrylamide on dry weight basis. The polyacrylamide was introduced less. The concentration of N (nitrogen) on the surface was as low as 1.3 atom %. This magnetic carrier was evaluated for nucleic acid extraction performance in the same manner as in Example 1. Table 2 shows the results. The nucleic acid extraction performance of this magnetic carrier was confirmed by the presence of the band of the intended size in the performance test. However, the detection ratio was as low as 20%, and the extraction performance was unstable.

From comparison of Comparative Example 3 with Examples, the lower amount of the introduced polyacrylamide gives lower efficiency of nucleic acid extraction.

Example 4

The magnetic carrier prepared in Example 1 was evaluated for performance of nucleic acid extraction from a pooled serum of HCV-infected persons as a practical sample. The method of evaluation was as below.

To 150 μL of pooled serum of HCV-infected persons, was added 300 μL of an extracting solid phase-containing liquid shown below. The mixture was stirred at room temperature for 12 minutes. Then the magnetic carrier was gathered to the corner of the vessel by use of a magnet, and the solution was removed by suction. The remaining gel was again suspended in 0.3 mL of washing solution (a mixture of isopropanol (40%) and an aqueous 0.33M KCl solution (60%)) added thereto. Then the gel was gathered again to the vessel corner with a magnet, and the solution was removed by suction. The magnetic carrier was suspended in 100 μL of elution solution (distilled water for injection), and the gel was gathered to the corner of the vessel, and 10 μL of the liquid from the bottom of the vessel was subjected to a reverse transcription reaction for conversion to a DNA. Thereto a polymerase solution was added to conduct PCR.

The aforementioned extracting solid phase-containing liquid, the composition of the reverse transcription reaction solution and the PCR reaction solution, and the temperature conditions for PCR are shown below.

The extracting solid phase-containing liquid was a 1:1 mixture of 6M guanidine thiocyanate/37.5 mM sodium citrate/magnetic carrier (1.2 mg/mL) and isopropanol. The reverse transcription was conducted with a nucleic acid of Sequence No. 3 (1.2 μM-HCV reverse primer), 4.5 mM $MgCl_2$, 3.4 mM NaCl, 1.4 mM dNTP, 0.87 mM DTT, 1.3 units/μL RNase inhibitor (produced by Takara Shuzo K.K.), and 2.0 units/μL MMLV RTase (produced by BRL Co.). Then PCR was conducted with a nucleic acid primer of Sequence No. 4 (240 nM-HCV forward primer), 2.2 mM $MgCl_2$, 0.29 mM dNTP, and 2.25 units/75 μL of Taq polymerase (Ampli Taq gold) by repeating the cycle of 95° C. for 20 seconds, and 60° C. for 30 seconds 45 times, and thereafter treating it at 72° C. for 60 seconds. After completion of the PCR, a part of the reaction solution was subjected to agarose electrophoresis and the presence of the band of the intended size was examined visually.

The above extraction test was repeated ten times. The ratio of detection of nucleic acid extraction (band of intended size) was shown as the detection ratio as a measure of the nucleic acid extraction.

Detection ratio (%)=[(Times of detection of extracted nucleic acid)/(Times of extraction tests)]×100

The results are shown in Table 2. The band of the intended size was detected, whereby the nucleic acid extraction performance was confirmed. The detection ratio was 100%, showing the reproducibility of the extraction with a practical sample.

The magnetic carrier of the present invention, which has acrylamide and/or polyacrylamide bonded uniformly onto the surface thereof, exhibits characteristic adsorption and extraction performances which are not shown by the particulate magnetic silica carrier itself. Furthermore, it is in a sphere shape, contains a sufficient amount of a magnetic material, and has high strength, so that it is useful as an adsorbent and an extractant. According to the process of the present invention, particulate magnetic silica can readily be produced which has a desired amount of acrylamide and/or polyacrylamide in correspondence with application fields. Further, a nucleic acid can readily be extracted by use of the magnetic carrier of the present invention with good reproducibility.

TABLE 1

|  | Example | | | Comparative Example | | |
| --- | --- | --- | --- | --- | --- | --- |
|  | 1 | 2 | 3 | 1 | 2 | 3 |
| Acrylamide content (mmol/g) | 2 | 1.4 | 3.5 | 0 | — | 0.2 |
| Amount of N atom on carrier surface (atom %) | 7.4 | 6.4 | 8 | 0 | — | 1.3 |
| Dissolved oxygen concentration in acrylamide reaction solution (mg/L) | 0.6 | 0.7 | 0.8 | — | — | 5.2 |
| Number-average molecular weight of polyacrylamide in solution | 120000 | 62000 | 520000 | — | — | Less than 1000 |
| Iron content (wt %) | 11 | 14 | 11 | 13 | 12 | 9 |
| Volume-average particle diameter ($\mu$m) | 7.4 | 5.2 | 12.3 | 8.2 | 8.0 | 5.1 |
| BET specific surface area (m$^2$/g) | 341 | 295 | 382 | 310 | 320 | 282 |
| Average pore diameter (nm) | 40 | 30 | 50 | 70 | 60 | 50 |
| Pore volume (mL/g) | 1 | 0.8 | 1.2 | 1.5 | 1.4 | 1.3 |

TABLE 2

|  | Example | | | Comparative Example | | | Example |
| --- | --- | --- | --- | --- | --- | --- | --- |
|  | 1 | 2 | 3 | 1 | 2 | 3 | 4 |
| Detection ratio in nucleic acid extraction test (%) | 100 | 100 | 100 | 20 | 0 | 20 | — |
| Detection ratio of nucleic acid extraction with practical sample (%) | — | — | — | — | — | — | 100 |

What is claimed is:

1. A magnetic carrier comprising particulate silica containing a magnetic material, having polyacrylamide on the surface thereof in an amount ranging from 0.3 to 5 mmol/g in terms of monomeric acrylamide.

2. The magnetic carrier according to claim 1 for adsorption-separation or extraction of a nucleic acid, wherein the magnetic carrier contains polyacrylamide in an amount ranging from 0.5 to 5 mmol/g in terms of monomeric acrylamide.

3. The magnetic carrier according to claim 1, wherein the amount of nitrogen atoms on the surface of the magnetic carrier is not less than 5 atom %.

4. A process for producing the magnetic carrier set forth in any of claims 1 to 3, comprising steps:

(a) providing particulate magnetic silica by addition of a magnetic material to silica or a silica source material;

(b) reacting the particulate magnetic silica after step (a) with a coupling agent;

(c) washing the particulate magnetic silica after step (b);

(d) reacting the particulate magnetic silica after step (c) with acrylamide and/or polyacrylamide; and (e) washing and drying the particulate magnetic silica after step (d).

5. The process for producing the magnetic carrier according to claim 4, wherein step (e) comprises washing, the particulate magnetic silica with water, whereafter water in the particulate magnetic silica is substituted for by an organic solvent, whereafter the organic solvent is removed by driving.

6. The process for producing the magnetic carrier according to claim 4, wherein, in step (d), dissolved oxygen concentration in the reaction solution containing the particulate magnetic silica and, acrylamide and/or polyacrylamide is controlled not higher than 1 mg/L.

7. The process for producing the magnetic carrier according to claim 5, wherein, in step (d), the polyacrylamide in the solution after the reaction has a number-average molecular weight ranging from 1,000 to 1,000,000.

* * * * *